US009488610B2

(12) United States Patent
Heppe

(10) Patent No.: US 9,488,610 B2
(45) Date of Patent: Nov. 8, 2016

(54) WEAVING METHOD FOR PRODUCING A PLURALITY OF MOISTURE SENSORS FOR A DEVICE FOR MONITORING A PATIENT ACCESS

(71) Applicant: Fresenius Medical Care Deutschland GmbH, Bad Homburg OT (DE)

(72) Inventor: John Heppe, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 682 days.

(21) Appl. No.: 13/623,287

(22) Filed: Sep. 20, 2012

(65) Prior Publication Data

US 2013/0075018 A1 Mar. 28, 2013

Related U.S. Application Data

(60) Provisional application No. 61/537,085, filed on Sep. 21, 2011.

(30) Foreign Application Priority Data

Sep. 21, 2011 (DE) .......................... 10 2011 113 838

(51) Int. Cl.
*B32B 38/00* (2006.01)
*G01N 27/04* (2006.01)
(Continued)

(52) U.S. Cl.
CPC .......... *G01N 27/048* (2013.01); *A61M 1/3653* (2013.01); *D03D 1/0088* (2013.01);
(Continued)

(58) Field of Classification Search
CPC ... G01M 3/16; G01N 27/048; D03D 1/0088; D03D 11/00; D03D 15/00
USPC ....................................................... 156/148
See application file for complete search history.

(56) References Cited

U.S. PATENT DOCUMENTS 4,210,041 A * 7/1980 Mitman ................. B21D 28/06
33/11
6,445,304 B1 9/2002 Bandeian, Jr. et al.
(Continued)

FOREIGN PATENT DOCUMENTS

DE 101 47 641 A1 4/2003
DE 10 2006 017340 A1 10/2006
(Continued)

OTHER PUBLICATIONS

International Preliminary Report on Patentability (IPRP) and Written Opinion in PCT/EP2012/003831, dated Mar. 25, 2014.
(Continued)

*Primary Examiner* — Philip Tucker
*Assistant Examiner* — John Blades
(74) *Attorney, Agent, or Firm* — Andrews Kurth Kenyon LLP

(57) ABSTRACT

A weaving method for producing a plurality of moisture sensors for a device for monitoring an access to a patient, in particular for monitoring the vascular access in an extracorporeal blood treatment, wherein the moisture sensors are woven. During the weaving of the moisture sensors, non-conductive warp threads, non-conductive weft threads, conductive warp threads and conductive weft threads are disposed in the textile two-dimensionally extending structure, such that spatially demarcatable structures of electrical strip conductors are created. The strip conductor structures can be produced by spatial separation or contacting of the conductive warp or weft threads. In order to be able to produce the moisture sensors cost effectively in large numbers, a plurality of individual moisture sensors are repeatedly woven each time beside one another normal to the production direction on a common woven fabric web as the web progressively advances, so that the width of the woven fabric web is occupied in the best possible way by as many moisture sensors as possible. The individual moisture sensors are separated from one another after weaving.

18 Claims, 9 Drawing Sheets

(51) Int. Cl.
*D03D 1/00* (2006.01)
*A61M 1/36* (2006.01)
*D03D 11/00* (2006.01)
*G01M 3/16* (2006.01)
*D03D 15/00* (2006.01)
*A61B 5/02* (2006.01)

(52) U.S. Cl.
CPC ............ *D03D 11/00* (2013.01); *D03D 15/00* (2013.01); *G01M 3/16* (2013.01); *G01M 3/165* (2013.01); *A61B 5/02042* (2013.01); *A61B 2562/029* (2013.01); *A61B 2562/12* (2013.01); *D10B 2401/16* (2013.01); *D10B 2509/00* (2013.01)

(56) References Cited

U.S. PATENT DOCUMENTS

| | | | |
|---|---|---|---|
| 2005/0038325 A1 | 2/2005 | Moll | |
| 2005/0122346 A1* | 6/2005 | Horn | G06F 17/50 345/629 |
| 2007/0089800 A1* | 4/2007 | Sharma | 139/388 |
| 2007/0240548 A1* | 10/2007 | Pape | B26D 5/00 83/76.1 |
| 2009/0145543 A1* | 6/2009 | Velasquez Urey | C09J 7/026 156/252 |

FOREIGN PATENT DOCUMENTS

| | | | |
|---|---|---|---|
| DE | 10 2009 013874 A1 | 9/2010 | |
| EP | 1 997 952 A2 | 12/2008 | |
| EP | 2 360 301 A1 | 8/2011 | |
| FR | 2 785 626 A1 | 5/2000 | |
| JP | 54 133 196 A | 10/1979 | |
| WO | 2006/008866 A1 | 1/2006 | |
| WO | 2009/075592 A2 | 6/2009 | |
| WO | WO 2010/091852 * | 8/2010 | .............. A61M 1/36 |

OTHER PUBLICATIONS

PCT International Search Report and Written Opinion from PCT/EP2012/003831 mailed on Dec. 12, 2012.

* cited by examiner

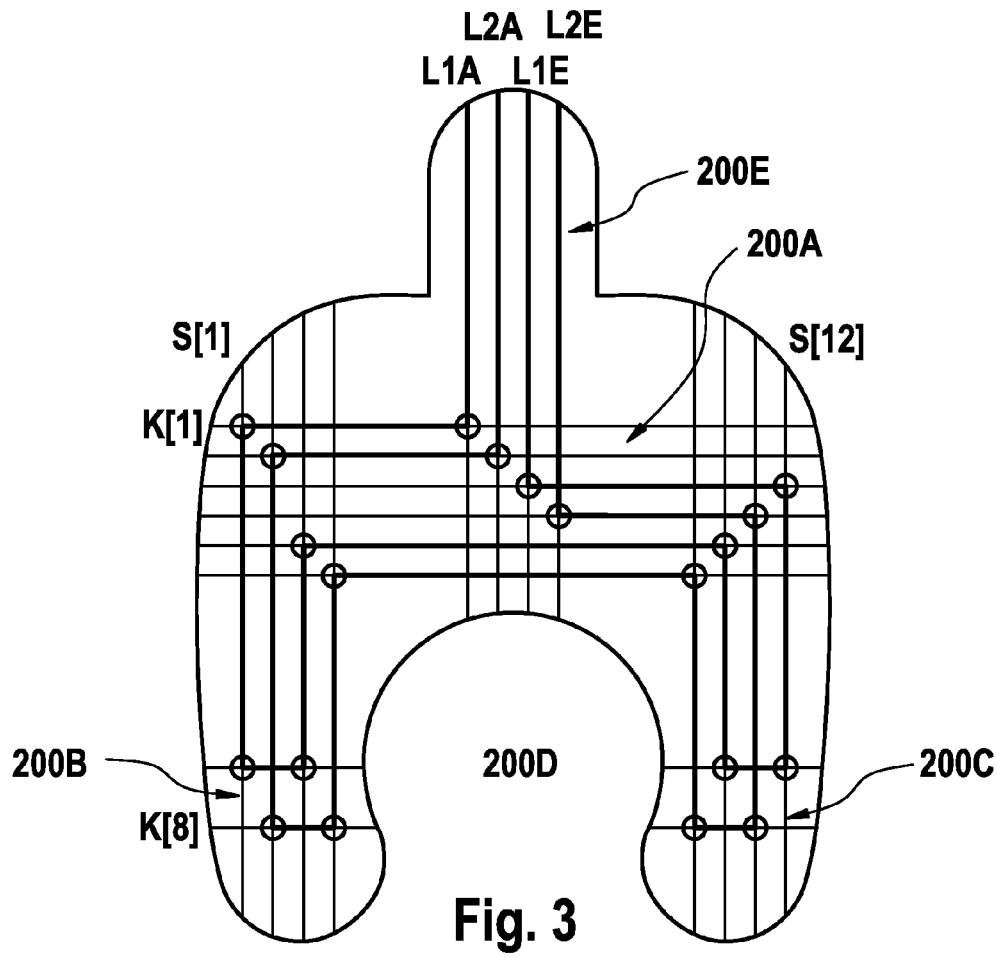

Fig. 3

| | | | | | L1A | L2A | L1E | L2E | | | | | |
|---|---|---|---|---|---|---|---|---|---|---|---|---|---|
| | S[1] | S[2] | S[3] | S[4] | S[5] | S[6] | S[7] | S[8] | S[9] | S[10] | S[11] | S[12] | |
| K[1] | Cont. | Isol. | Isol. | Isol. | Cont. | Isol. | Isol. | Isol. | Isol. | Isol. | Isol. | Isol. | |
| K[2] | Isol. | Cont. | Isol. | Isol. | Isol. | Cont. | Isol. | Isol. | Isol. | Isol. | Isol. | Isol. | |
| K[3] | Isol. | Isol. | Isol. | Isol. | Isol. | Isol. | Cont. | Isol. | Isol. | Isol. | Isol. | Cont. | |
| K[4] | Isol. | Isol. | Isol. | Isol. | Isol. | Isol. | Isol. | Cont. | Isol. | Isol. | Cont. | Isol. | |
| K[5] | Isol. | Isol. | Cont. | Isol. | Isol. | Isol. | Isol. | Isol. | Isol. | Cont. | Isol. | Isol. | |
| K[6] | Isol. | Isol. | Isol. | Cont. | Isol. | Isol. | Isol. | Isol. | Cont. | Isol. | Isol. | Isol. | |
| K[7] | Cont. | Isol. | Cont. | Isol. | | | | | Isol. | Cont. | Isol. | Cont. | |
| K[8] | Isol. | Cont. | Isol. | Cont. | | | | | Cont. | Isol. | Cont. | Isol. | Σ |
| Sum Cont. | 2 | 2 | 2 | 2 | 1 | 1 | 1 | 1 | 2 | 2 | 2 | 2 | 20 |
| Sum Isol. | 6 | 6 | 6 | 6 | 5 | 5 | 5 | 5 | 6 | 6 | 6 | 6 | 68 |

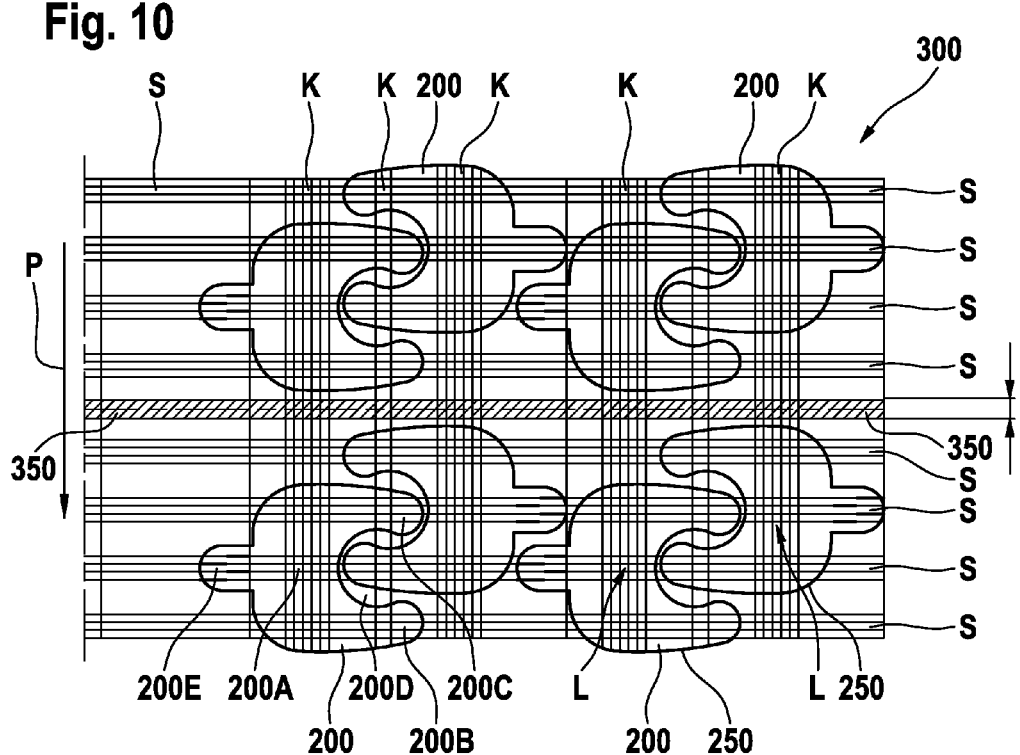
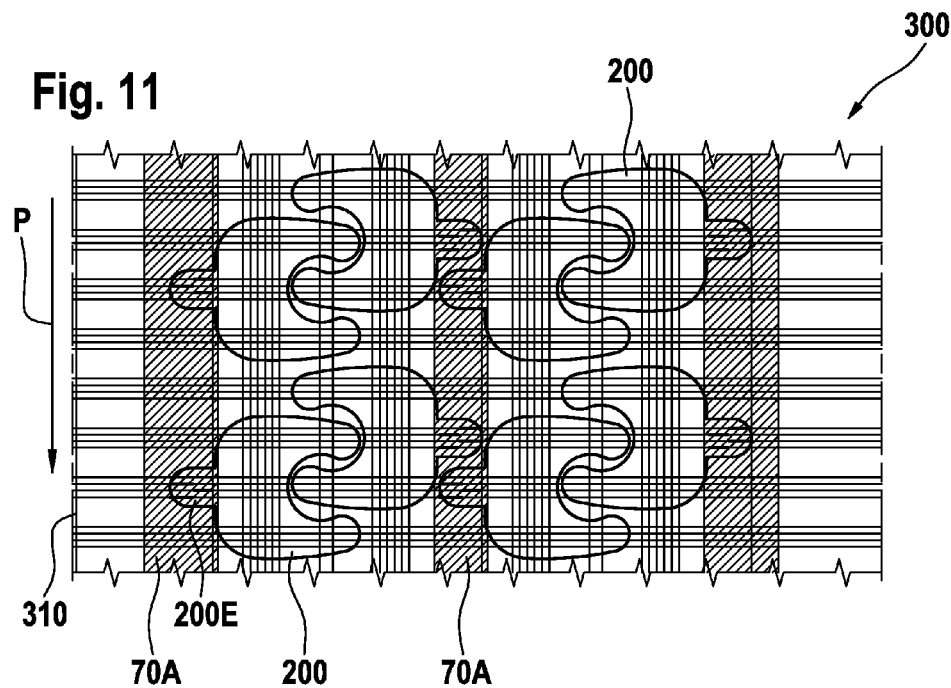

WEAVING METHOD FOR PRODUCING A PLURALITY OF MOISTURE SENSORS FOR A DEVICE FOR MONITORING A PATIENT ACCESS

CROSS REFERENCE TO RELATED APPLICATIONS

The present application claims priority to U.S. Provisional Application Ser. No. 61/537,085, filed on Sep. 21, 2011, and claims priority to Application No. DE 10 2011 113 838.6, filed in the Federal Republic of Germany on Sep. 21, 2011, each of which is expressly incorporated herein in its entirety by reference thereto.

FIELD OF INVENTION

The present invention relates to a weaving method for producing a plurality of moisture sensors for a device for monitoring an access to a patient, in particular for monitoring the vascular access in an extracorporeal blood treatment, wherein a patient's blood is removed from the patient via an arterial hose line, which comprises an arterial cannula, and is fed to the patient via a venous hose line, which comprises a venous puncture cannula.

BACKGROUND INFORMATION

In the field of medical technology, various apparatuses are known with which fluid can be withdrawn from patients or fluids can be fed to patients via a hose line. The access to the patient generally takes place with a catheter for introduction into body organs or a cannula for the puncturing of vessels. During the examination or treatment, a correct access to the patient must be ensured. It is therefore necessary to monitor the patient access. A correct access to the patient is required in particular by extracorporeal blood treatment apparatuses comprising an extracorporeal blood circuit.

Devices for monitoring a vascular access are known, which comprise a moisture sensor in order to be able to detect the issuing of blood at the puncture point. The known moisture sensors are constituted as a pad which is to be placed on the puncture point. International Patent Publication No. WO 2006/008866 A1, U.S. Patent Publication No. US 2005/0038325 A1 and U.S. Pat. No. 6,445,304 describe moisture sensors comprising an absorbent material in which an electrically conductive structure is embedded. The detection of moisture is based on the measurement of the electrical resistance between the strip conductors.

International Patent Publication No. WO 2009/075592 A2 describes a moisture sensor in the form of a strip of woven fabric on which or in which two parallel strip conductors are provided, between which the electrical resistance is measured. The two strip conductors are formed by conductive yarns which run only in the longitudinal direction of the strip of woven fabric. Electrical contact points between intersecting strip conductors are not provided.

SUMMARY

A problem underlying the present invention is to provide a weaving method with which moisture sensors can be produced cost-effectively in large numbers for a device for monitoring a patient access.

The method according to the present invention for producing a plurality of moisture sensors is characterized in that the moisture sensors are woven. During the weaving of the moisture sensors, non-conductive warp threads and non-conductive weft threads as well as conductive warp threads and conductive weft threads are disposed in the textile two-dimensionally extending structure, in such a way that spatially demarcatable structures of electrical strip conductors are created. The strip conductor structures can be produced by spatial separation or contacting of the conductive warp or weft threads.

In order to be able to produce moisture sensors in large numbers in a cost-effective manner, a plurality of individual moisture sensors are repeatedly woven each time beside one another normal to the production direction on a common woven fabric web as the web progressively advances, so that the width of the woven fabric web is occupied in the best possible way by as many moisture sensors as possible. The individual moisture sensors are separated from one another after weaving and any further processing steps.

Since a plurality of moisture sensors can be produced in one work cycle, the production of moisture sensors is associated with relatively low production costs. The production process can take place with a high degree of automation.

In principle, it is unimportant for the weaving method according to the present invention how the strip conductor structures are created from conductive warp and/or weft threads. In principle, it is also unimportant for the method according to the present invention how the spatially demarcatable structures of electrical strip conductors are disposed on the common woven fabric web.

It has however been shown in practice that the arrangement of the moisture sensors with the spatially demarcatable strip conductor structures is of importance insofar as a particular arrangement of the moisture sensors and the strip conductor structures permits a particularly efficient production of the moisture sensors.

Some advantageous exemplary embodiments of the present invention relate to the special arrangement of the moisture sensors with the strip conductor structures on the woven fabric web.

Moreover, it is important for particularly efficient production of the moisture sensors that the individual moisture sensors can be separated from one another without the strip conductor structures being destroyed.

Some advantageous exemplary embodiments of the method according to the present invention enable an exact separation of the individual moisture sensors.

The present invention also relates to a device for weaving, with which the weaving method according to the present invention can be implemented.

A preferred exemplary embodiment of the method according to the present invention makes provision such that a compensation strip running normal to the production direction is woven between a preceding group of moisture sensors, which are woven beside one another normal to the production direction, and a subsequent group of moisture sensors, which are woven beside one another normal to the production direction.

Locally different kinds of weave are used in the weaving in the regions of the woven fabric web with the moisture sensors. Locally different changes in length of the threads thus arise. These changes in length in turn cause stresses in the woven fabric.

The occurrence of stresses in the woven fabric can be prevented with the compensation strips. A compensation strip is understood to mean a region on the woven fabric web which comprises only one constant kind of weave, for example an atlas weave or a plain weave. Mechanical stresses between the threads can be compensated for or assimilated in the compensation strips. It is thus possible to dispose moisture sensors in the woven fabric in a great density without their being the risk of the exact mutual alignment of the moisture sensors with the strip conductors being lost, this being of great importance for the production of the sensors.

In a preferred exemplary embodiment, the spatial arrangement of the moisture sensors takes place in an interlaced manner, if the outer contour of the sensors permits an interlaced arrangement. It is thus possible to weave together a particularly large number of moisture sensors in lines and columns with a particularly small spacing, so that a particularly large number of moisture sensors can be produced in a work cycle.

The intersecting conductive warp threads and weft threads are preferably disposed for the formation of the strip conductor structures in such a way that the warp and weft threads make contact at individual points of intersection. The strip conductor structures of the individual moisture sensors are preferably formed from groups of conductive warp threads, which each comprise a plurality of conductive warp threads running in a first direction, and groups of conductive weft threads, which each comprise a plurality of conductive weft threads running in a direction at right angles to the first direction. The groups of warp threads are disposed with an equal spacing from one another and/or the groups of weft threads are disposed with an equal spacing from one another. A largely symmetrical structure thus arises, but one which still permits an offset or interlaced arrangement of the moisture sensors, when the moisture sensors have a shape corresponding to the created structure.

The moisture sensors each comprise an inner region with two legs, which laterally surround a central cutout. A preferred exemplary embodiment makes provision such that the moisture sensors each comprise tabs at which the strip conductors form terminal contacts. The moisture sensors can be disposed offset with respect to one another, in such a way that in each case a leg of a moisture sensor engages in a cutout of another moisture sensor. The lateral offset of the moisture sensors corresponds to the spacing of the individual groups of warp and weft threads, with which the strip conductors are formed on the central region and the two legs of the moisture sensors.

With the interlaced arrangement of the moisture sensors, it is advantageous if the sensors are constituted such that sensors disposed in each case beside one another have a common outer contour at least over a partial region. The moisture sensors can preferably be disposed offset with respect to one another, in such a way that a leg of a sensor in each case engages into a section of another sensor, wherein the interlaced moisture sensors have a common outer contour in the region of the cutout or in the region of the leg. A gaplessly interlaced arrangement of the moisture sensors thus arises, which is characterized by an optimized cut-edge length. The minimized cut-edge length leads to a time-saving on cutting, especially laser cutting, and a reduced waste of material, wherein two sensors can be separated from one another with only one cut in the region concerned.

In the exemplary embodiment of the moisture sensors with the central region and the two legs, the strip conductor structures are preferably formed in each case by three groups of weft threads and two groups of warp threads. The groups of weft threads preferably comprise the same number of weft threads, whereas the groups of warp threads comprise a different number of warp threads. The symmetrical structure of the preferred embodiment of the moisture sensors makes it possible for the groups of weft threads to be disposed with an equal spacing from one another. Instead of weft threads, warp threads can however also be provided or vice versa.

Marking elements running normal to the production direction and/or cross-shaped marking elements, which are disposed between the moisture sensors, are preferably used to mark the positions of the moisture sensors on the woven fabric web. Precise marking and recognition of the position of the moisture sensors is not only essential when separating the moisture sensors, but is also required when a further layer is to be applied on the woven fabric web in exact alignment with the moisture sensors and strip conductor structures. It has been shown in practice that the production of sensors in large numbers on a common weaving web can be achieved only with the weaving of marking elements.

In a preferred exemplary embodiment, the layer to be applied on the woven fabric web is used to create a separation layer and/or an adhesive layer. With the separation layer, a barrier can be created against saturation of the woven fabric, whilst the moisture sensor can be fixed on the patient's skin with the adhesive layer. The layer preferably comprises a two-sided adhesive film, which is provided on one side with a tear-off film (liner).

The marking elements are preferably formed by conductive warp and/or weft threads, which differ in color from the non-conductive warp and weft threads. The conductive warp and/or weft threads which form the marking elements are preferably laid on the surface of the woven fabric, so that they can be seen more easily. If conductive warp and/or weft threads are not to be present at the point to be marked, the marking elements can also be formed by contrast-rich threads which are non-conductive.

The intersecting conductive warp and weft threads or contrast-rich non-conductive threads also permit the creation of marking elements that can be used as control points.

The marking elements or control points are preferably disposed in the region of the woven fabric web in which the moisture sensors are not present. The marking elements can however also be located in the moisture sensors or extend through the moisture sensors if the strip conductor structures are not thereby destroyed.

An example of an embodiment of a blood treatment apparatus, which comprises a device for monitoring the arterial and venous vascular access, as well as an example of an embodiment of the moisture sensor, which is used in the device for monitoring the patient access, are explained in greater detail below. Moreover, the method according to the present invention for producing the moisture sensors for the device for monitoring the patient access is described in detail below.

BRIEF DESCRIPTION OF THE DRAWINGS

FIG. 3 shows an example of an embodiment of the moisture sensor according to the present invention in a schematic representation.

FIG. 4 shows a matrix to illustrate the points of intersection of the warp and weft threads of the device for detecting moisture from FIG. 3.

FIGS. 6A to 6E show a representation to illustrate the linkages between warp and weft threads of the device from FIG. 3 in the cross-sectional planes from FIG. 5.

FIG. 10 shows the woven fabric web with the moisture sensors, wherein a compensation strip is disposed between the moisture sensors.

FIG. 11 shows a representation to illustrate the adhesive-free zones of the adhesive film to be lined with the woven fabric web.

DETAILED DESCRIPTION

Figure 1:
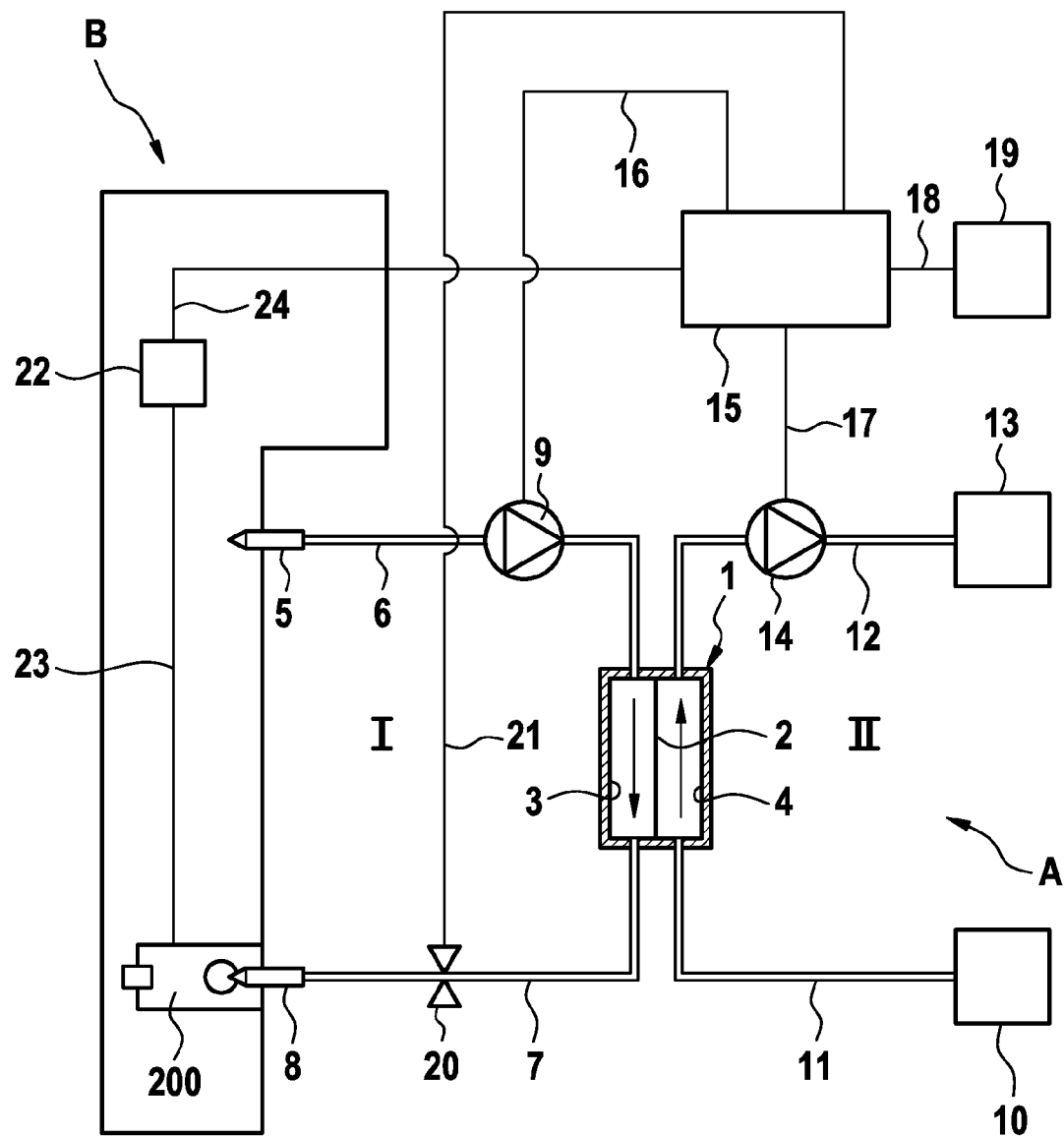
FIG. 1 shows the main components of a blood treatment apparatus, which comprises a device for monitoring the arterial and venous vascular access.

FIG. 1 shows the main components of a blood treatment apparatus, in particular hemodialysis apparatus A, which comprises a device B for monitoring the arterial and venous vascular access. In the present example of an embodiment, monitoring device B is a component part of hemodialysis apparatus A. The dialysis apparatus will first be described by reference to FIG. 1.

Hemodialysis apparatus A comprises a dialyzer 1, which is divided by a semipermeable membrane 2 into a blood chamber 3 and a dialyzing fluid chamber 4. An arterial hose line 6 is connected by means of an arterial puncture cannula 5 to the fistula or the shunt of the patient, said arterial hose line leading to the inlet of the blood chamber of the dialyzer. Leading away from the outlet of blood chamber 3 of dialyzer 1 is a venous hose line 7, which is connected by means of a venous puncture cannula 8 to the fistula or the shunt of the patient. A blood pump 9, which conveys the blood in extracorporeal blood circuit I, is incorporated into arterial hose line 6. Dialyzing fluid circuit II of dialysis apparatus A comprises a dialyzing fluid source 10, to which a dialyzing fluid supply line 11 is connected, which leads to the inlet of dialyzing fluid chamber 4 of the dialyzer. Departing from the outlet of dialyzing fluid chamber 4 of dialyzer 1 is a dialyzing fluid discharge line 12, which leads to a drain 13. A dialyzing fluid pump 14 is incorporated into dialyzing fluid discharge line 12.

The control of the dialysis apparatus is assumed by a central control unit 15, which controls blood pump and dialyzing fluid pump 9, 14 via control lines 16, 17. Central control unit 15 is connected via a data line 18 to an alarm unit 19, which emits an optical and/or acoustic and/or tactile alarm in the event of a malfunction. Located downstream of blood chamber 3 of dialyzer 1 on venous hose line 7 is an electro-magnetically actuated hose clamp 20, which is closed via a further control line 21 to central control unit 15.

In the present example of an embodiment, monitoring device B is used to monitor the venous vascular access. Monitoring device B comprises a moisture sensor 200, which is disposed at the puncture point. Moisture sensor 200 is represented only schematically in FIG. 1. Moreover, the monitoring device also comprises an evaluation unit 22 which is connected electrically via a connection line 23 to moisture sensor 200.

Evaluation unit 22 is connected via a data line 24 to central control unit 15 of dialysis apparatus A. In the event of blood issuing from the venous cannula and/or the puncture point and moistening the moisture sensor, evaluation unit 22 generates a control signal, which is received by central control unit 15, which undertakes an intervention into the blood treatment. Control unit 15 stops blood pump 9 and closes hose clamp 20. Moreover, the control unit generates an alarm signal, so that alarm unit 19 emits an acoustic and/or optical and/or tactile alarm.

A first example of an embodiment of moisture sensor 200 to be placed on the patient's skin at the puncture point is described below. Moisture sensor 200 is constituted as a pad of a textile two-dimensionally extending fabric (woven fabric) to be placed on the patient's skin. In the first example of an embodiment, textile two-dimensionally extending fabric 100 is a multi-layer woven fabric.

Figure 2:
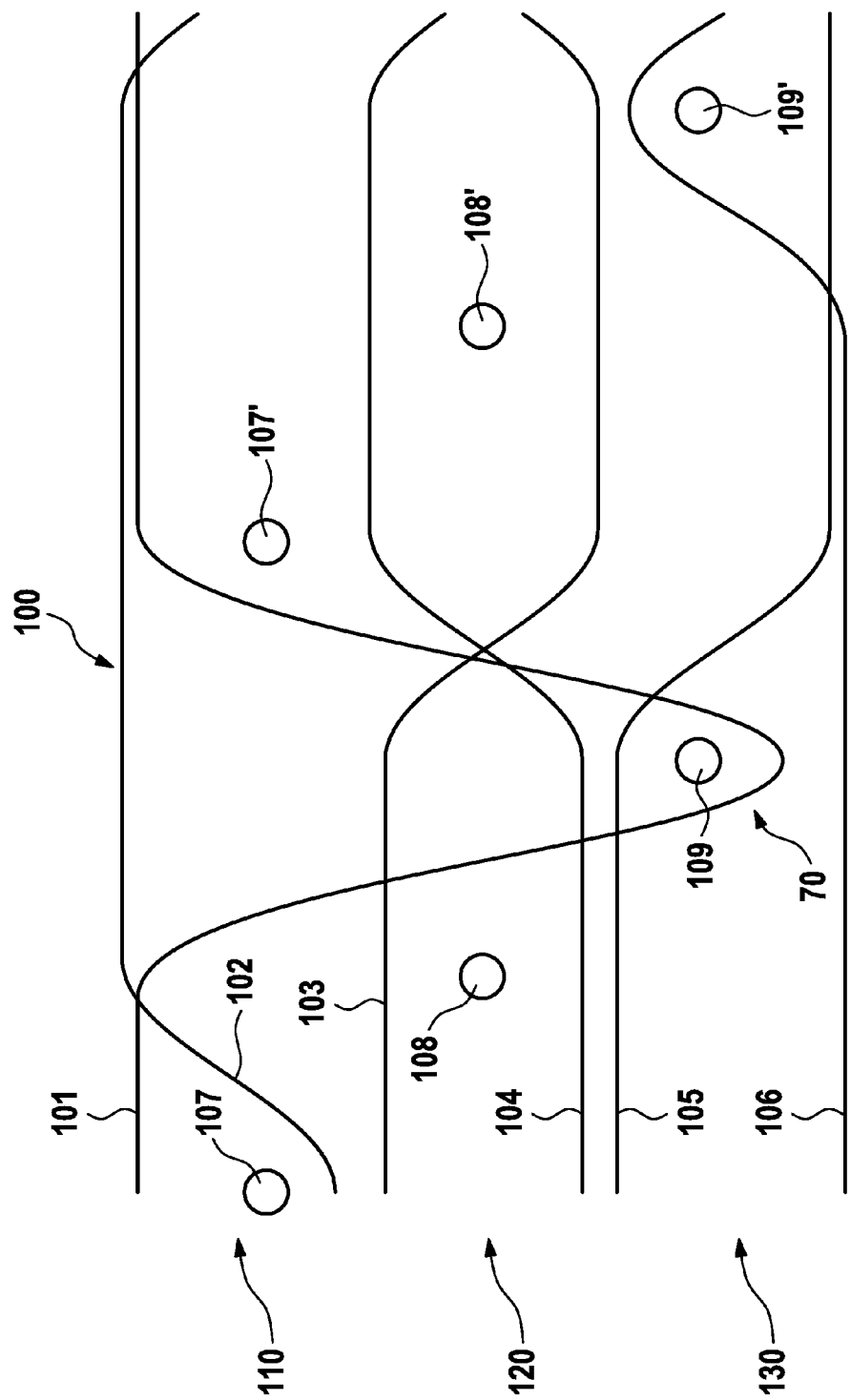
FIG. 2 shows a cross-section through the woven fabric of a moisture sensor according to the present invention.

FIG. 2 shows a warp section through multi-layer woven fabric 100. The warp threads running from left to right are represented in FIG. 2. The warp section shows a total of 6 warp threads 101 to 106. The number of layers of the woven fabric is defined according to the number of planes 110, 120, 130 in which weft threads 107, 108, 109; 107', 108', 109' lie. Weft threads 107, 108, 109; 107', 108', 109' lying essentially at right angles to the warp threads in the three planes 110, 120, 130 are marked by circles. The production of a three-layer woven fabric is known to the person skilled in the art. During weaving, weft threads 107, 108, 109; 107', 108', 109' lie on three planes 100, 110, 120. Warp threads 101 to 106 are fed on three planes. Each individual warp thread can be respectively raised or lowered out of the three warp thread planes in order to enable the interweaving of a weft thread. Out of originally 60 threads/cm, on one plane, 20 threads are fed in an upper plane, 20 threads are fed in a middle plane and 20 threads are fed in a lower plane in production in the case of the multi-layer woven fabric. The number of 60 threads/cm represents a common example, but can also diverge from this.

In the weaving process, weft threads 107, 108, 109; 107', 108', 109' do not necessarily have to be fed in planes lying above one another, but rather the position of a weft thread in a plane can also arise in the weaving process through the raised or lowered warp threads, which automatically pull the weft thread into a defined plane. The planes are always to be understood as "imaginary" layers which do not have to be "flat."

The multi-layer woven fabric is made from electrically conductive and electrically non-conductive warp and weft threads (monofilaments, carbon fibers, silvered polyamide yarn). The electrically conductive and electrically non-conductive warp and weft threads are disposed in such a way that the woven fabric comprises a lower layer facing the patient's skin, a middle layer and an upper layer facing away from the patient's skin. The division of the woven fabric into a plurality of layers, however, serves merely for a better understanding of the woven fabric structure, because in practice the layers cannot be precisely separated from one another.

A structure of electrical strip conductors is formed in the middle and upper plane of the woven fabric by the fact that the electrically conductive warp and weft threads are disposed at the points of intersection in such a way that they are either connected to one another in an electrically conductive manner or are insulated from one another electrically. A contact point between electrically conductive warp and weft threads can be achieved by means of a partial change of plane of the warp thread during the weaving process, as can be seen from FIG. 2.

FIG. 2 shows weft threads 107, 108, 109; 107', 108', 109' lying in three planes 110, 120, 130. As a result of the partial change of electrically conductive warp thread 102, for example from upper plane 110 into lower plane 130, an electrical connection is produced between this warp thread 101 and electrically conductive weft thread 109 in the lower plane that crosses warp thread 102. Without the partial change of planes, electrically conductive warp and weft threads are insulated from one another. For example, electrically conductive warp thread 102 is not electrically connected to electrically conductive weft thread 109, since warp thread 102 does not partially change plane in the region of weft thread 109.

FIG. 3 shows an example of an embodiment of the moisture sensor according to the present invention in a schematic representation. The moisture sensor comprises a central zone 200A with two legs 200B, 200C, which laterally enclose a semicircular cutout 200D. A tab 200E lying opposite the two legs is formed on the central zone.

The electrically conductive warp and weft threads forming a structure of electrical strip conductors are characterized by horizontal and vertical thin lines. Weft threads S run in the vertical direction and warp threads K run in the horizontal direction. The strip conductor structure is formed by eight warp threads K [1] to K [8] and twelve weft threads S [1] to S [12], which are disposed at the points of intersection in such a way that they are either connected in an electrically conductive manner or are insulated electrically from one another.

FIG. 4 shows a matrix to illustrate the 88 points of intersection of the 8 warp threads K [1] to [8] and 12 weft threads S [1] to S [12]. The points of intersection of two conductive threads which produce a contact are denoted in the matrix by "Cont.", whilst the points of intersection of two conductive threads which form an insulation point are denoted by "Isol.". An electrically conductive structure arises, which comprises two strip conductors which each form a conductor loop constituted non-redundant.

In FIG. 3, the electrical contact points at the points of intersection between the electrically conductive warp and weft threads K[i], S [i] are represented as circles. First strip conductor L1A-L1E runs from tab 200E via central zone 200A to left-hand leg 200B and from the left-hand leg via the central zone to right-hand leg 200C and from the right-hand leg via the central zone back to the tab of the pad. The start of the respective strip conductor is designated by "A" and the end of the strip conductor is designated by "E". The two ends L1A, L1E of first strip conductor L1A-L1E form the two terminal contacts. Second strip conductor L2A-L2E runs from tab 200E via central zone 200A to left-hand leg 200B and from the left-hand leg via the central zone to right-hand leg 200C and from the right-hand leg via the central zone to the tab of pad 40. The two ends L2A, L2E of second strip conductor L2A-L2E form the second pair of terminal contacts. The terminal contacts are disposed on tab 200E in such a way that terminal contacts L2A and L1E lie between terminal contacts L1A and L2E.

Figure 5:
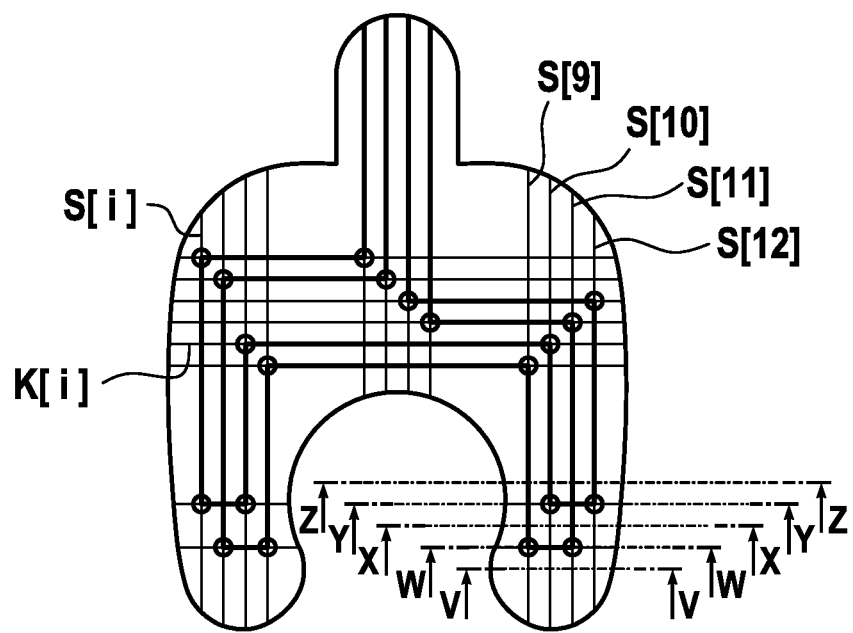
FIG. 5 shows a representation to illustrate various sections through the device from FIG. 3.

FIGS. 6A to 6E show the linkages of the warp and weft threads of the pad in the sectional planes, which are represented in FIG. 5. The warp threads K [i] and weft threads S [i] are not linked in sectional plane V-V, since warp threads are not present in this plane. Warp thread K [8] is linked to weft thread S [9] and warp thread K [8] is linked to weft thread S [11] in sectional plane W-W, so that an electrical connection is produced between warp and weft thread. Warp threads K [i] and weft threads S [i] are not linked in sectional plane X-X, since warp threads are not present in this plane. Warp thread K [7] is linked to weft thread S [10] and warp thread K [7] is linked to weft thread S [12] in sectional plane Y-Y, so that an electrical connection is produced between warp and weft thread. Warp threads K [i] and weft threads S [i] are not linked in sectional plane Z-Z, since warp threads are not present in this plane.

Figure 7:
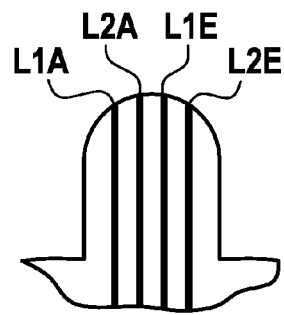
FIG. 7 shows an example of an embodiment of the tab of the moisture sensor.

FIG. 7 shows in a schematic representation the arrangement of terminal contacts L1A, L1E and L2A, L2E on tab 200E of the exemplary embodiments of the pad described above. In these embodiments, the ends of the warp or weft threads run with an identical spacing up to the edge of the tab. The threads are located at the surface of tab 200E in order to form terminal contacts L1A, L1E and L2A, L2E. In order to avoid a short circuit between the terminal contacts of the connection part, the width or the diameter of the terminal contacts of the connection part must be smaller than the distance between terminal contacts L1A and L2A, L2A and L1E as well as L1E and L2E of the pad. The width or the diameter of the terminal contacts of the connection part is therefore limited.

Figure 8:
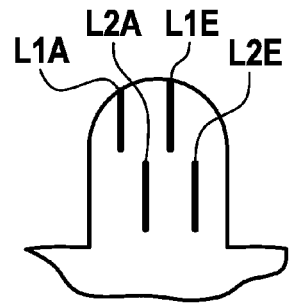
FIG. 8 shows a further example of an embodiment of the tab of the moisture sensor.

FIG. 8 shows an alternative embodiment of the arrangement of the terminal contacts on tab 200E of the pad in a schematic representation, wherein terminal contacts L1A and L1E of the one strip conductor L1A-L1E are disposed offset with respect to terminal contacts L2A and L2E of the other strip conductor L2A-L2E. Terminal contacts L1A and L1E of the one strip conductor are located on the upper half and terminal contacts L2A and L2E of the other strip conductor are located on the lower half of tab 200E. Since the pad comprises an insulating woven-fabric cover layer at the surface, a targeted "dipping" of the threads is possible. In the exemplary embodiment of FIG. 8, weft threads S [5] and S [7] (FIG. 3) lie in the—in FIG. 8—upper half of the tab beneath the cover layer and weft threads S [6] and S [8] (FIG. 3) lie in the lower half of the tab beneath the cover layer, so that the terminal contacts of the connection part can have a greater width or a greater diameter than in the case of the exemplary embodiment of FIG. 7, without a short circuit occurring between contacts L1A and L1E and respectively L2A and L2E.

The weaving method according to the present invention for producing the moisture sensors is described in detail below.

Figure 9:
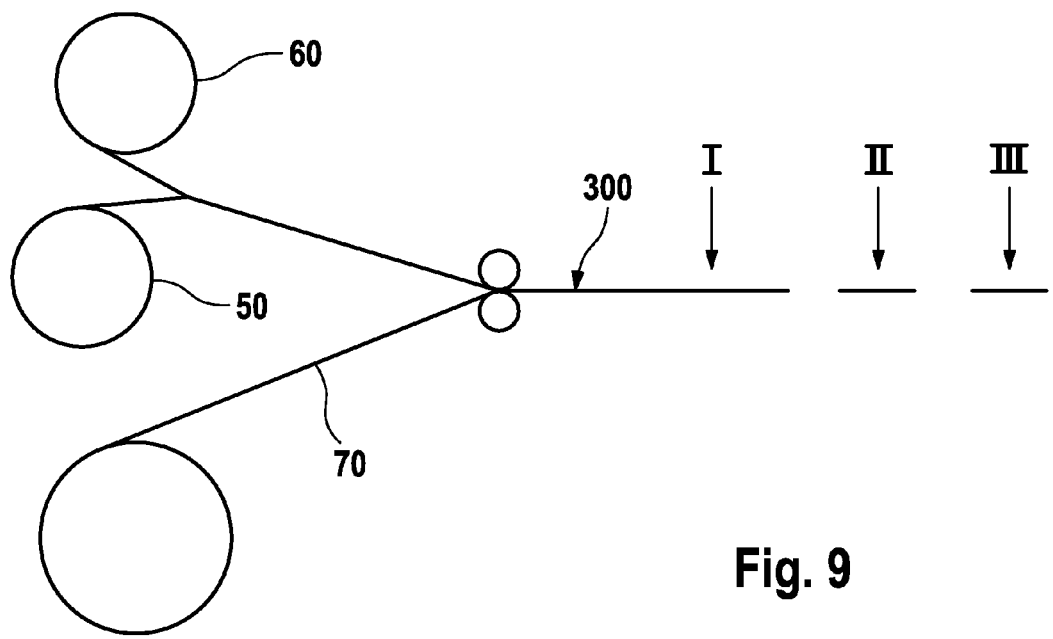
FIG. 9 shows a very simplified schematic representation of the process steps for producing the moisture sensors in accordance with the method according to the present invention.

FIG. 9 shows the main process steps for the production of the moisture sensors in a very simplified schematic representation. Warp threads 50 and weft threads 60 are fed for the production of preferably multi-layer woven fabric 200. After the production of the woven fabric, further process steps known to the person skilled in the art take place, which however are not described. They include, for example, finishing, in particular washing, fixing or a heat treatment.

During the weaving process, a layer 70 is fed, with which the woven fabric web is lined. Layer 70 is applied on the underside of woven fabric web 80. The individual moisture sensors are then separated in a further process step I. The moisture sensors are examined in a further process step II. Finally, the sensors are packaged III.

Apart from the electrical properties, the wetting behavior is decisive for the function of the moisture sensors. It has been shown in tests that the wetting behavior of the moisture sensors can be favorably influenced with spinning preparations (softening). Without spinning preparations, the moisture sensors exhibit a hydrophobic behavior. With the method according to the present invention, therefore, threads 50, 60 are provided with a spinning preparation, so that a hydrophilic behavior is exhibited.

Different warp thread lengths per unit of length arise through the different raising and lowering of the warp threads, which leads to different kinds of linkage in the woven fabric. The warp threads (x warp threads) with a length (y m) are wound on a warp beam, before the warp threads are processed in the weaving machine.

Stresses in the warp threads or in the woven fabric arise due to the different lengths. In order to be able to compensate for these stresses, compensation strips 350 are woven into the woven fabric after a specific path section, i.e., after the weaving of one or more lines with moisture sensors disposed beside one another. The width of compensation strips 350 and the spacing of successive compensation strips are dimensioned such that the stresses present in the warp threads are removed.

FIG. 10 shows a section of woven fabric web 300 for the production of moisture sensors 200. Production direction P of the woven fabric web is marked with an arrow. Weft threads S and warp threads K for producing moisture sensors 200 are again represented by lines. Weft threads S run normal to the production direction, whereas warp threads K run in the production direction. Weft and warp threads S, K form a kind of grid, into which the contours of the moisture sensors are inserted. FIG. 10 shows that compensation strips 350 run between moisture sensors 200 over the whole width of the woven fabric web normal to the production direction.

The arrangement of the moisture sensors and the electrically conductive warp and weft threads is described in detail below.

A plurality of moisture sensors 200 are woven beside one another on woven fabric web 300 normal to production direction P, i.e., over the whole width of the woven fabric web. FIG. 10 shows a usable zone of the woven fabric web. In practice, the woven fabric web has a width of 1000 mm, the woven fabric web being divided into three usable zones each having a width of 306 mm. Four moisture sensors are disposed beside one another on one usable zone. This results in twelve sensors being disposed in a row.

In the present example of an embodiment, four moisture sensors are in each case woven beside one another normal to the production direction, the moisture sensors being disposed interlaced with respect to one another. A total of eight interlaced moisture sensors thus form a preceding group of sensors, which are woven beside one another normal to the production direction, and eight interlaced moisture sensors form a subsequent group of moisture sensors which are woven beside one another normal to the production direction. Compensation strip 350 runs between the two groups of sensors.

The individual moisture sensors of a group of moisture sensors are disposed offset with respect to one another in such a way that in each case a leg 200B, 200C of a moisture sensors 200 engages in a cutout 200D of another moisture sensor. Moisture sensors 200 thus lie closely beside one another without making contact.

FIG. 10 shows that contours of the moisture sensors are orientated on the grid of threads S, K or vice versa. Weft threads S running normal to the production direction form in each case, with an equal spacing, successive groups of weft threads, which each comprise four weft threads disposed at an equal distance from one another. The two outer groups of weft threads S run through the central region of one of the two legs 200B, 200C of the one moisture sensor 200 and through tab 200E and central region 200A as well as cutout 200D of the other moisture sensor, which is interlaced with the aforesaid sensor, whilst the middle groups of weft threads S run through tab 200E and central region 200A as well as cutout 200D of the one moisture sensor 200 and the central region of one of the two legs 200B, 200C of the other moisture sensor.

Warp threads K running in production direction P form two groups, which comprise the same number of warp threads, and a group which comprises a smaller number of warp threads. The groups with the larger number of warp threads extend through central region 200A of moisture sensors 200, whilst the groups with the smaller number of warp threads extend through legs 200B, 200C of the moisture sensors. The warp and weft threads thus run in each case at right angles to one another, so that points of intersection arise at which the contacting of the warp and weft threads can take place (FIG. 3).

FIG. 10 shows that, with a largely symmetrical division of warp and weft threads running normal to one another without interruptions, strip conductor structures L that have a predetermined contour 250 can be created on moisture sensor 200, wherein the moisture sensors can be separated from one another again without destroying the electrically conductive structures. The production costs can be reduced with this offset or interlaced arrangement.

The application of layer 70 on woven fabric web 300 is described in detail below by reference to FIG. 11. Woven fabric web 300 comprises a rear side facing the patient and a front side facing away from the patient. Layer 70 is an adhesive film which is provided with a tear-off film (liner). The adhesive film also comprises a rear side facing the patient and a front side facing away from the patient. The adhesive film is provided with an adhesive layer at the front and rear side. The front side of the adhesive film is glued to the rear side of the woven fabric web (FIG. 9). The adhesive layer on the rear side of the two-sided adhesive film is protected by the tear-off film, which is torn off and discarded before the application of the moisture sensor on the patient's skin. The upper adhesive layer and the lower adhesive layer of the adhesive film can have different properties. The upper adhesive layer is intended to connect the woven fabric web and the adhesive film firmly together, whilst the lower adhesive layer is used only for the adhesion of the sensor to the patient's skin. The adhesive film (layer) provided with the tear-off film is also referred to below as adhesive film 70 for the sake of simplicity.

The adhesive layer at the underside of adhesive film 70 comprises regions which are free from adhesive. These regions are zones 70A running in production direction P, which are shaded in FIG. 11. These adhesive-free zones 70A are intended to lie beneath terminal tabs 200E of moisture sensors 200 during the lamination of woven fabric web 300 and adhesive film 70, since the moisture sensor should not adhere to the patient's skin in the region of tab 200E, but otherwise should adhere completely to the patient's skin. Exact alignment of the adhesive-free zones and the tabs of the sensors is required for this.

For the exact alignment of adhesive-free zones 70A and terminal tabs 200E, use is made of marking elements 310 running in production direction P, said marking elements being able to be conductive warp threads K which are laid at the surface of the woven fabric, so that the warp threads stand out visually from the woven fabric. A zero line 310 is thus created. Alternatively, the marking elements can also be formed with contrast-rich threads that are not conductive.

Figure 12:
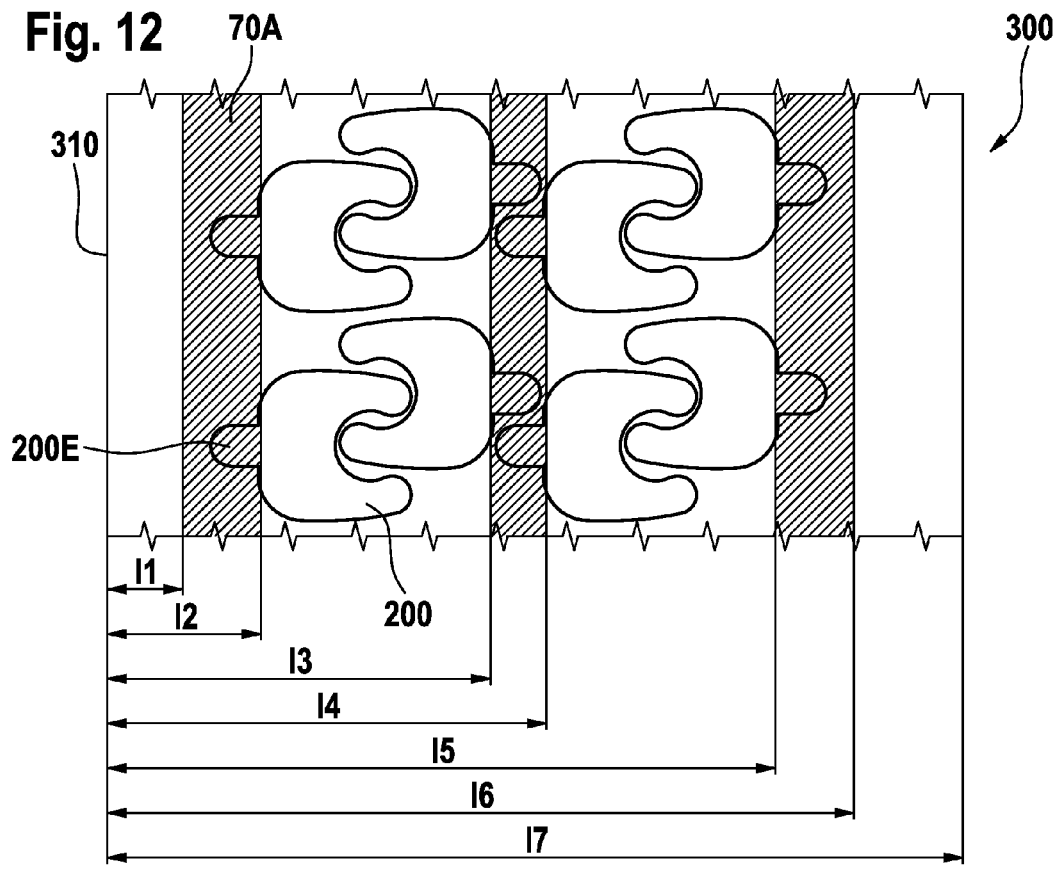
FIG. 12 shows a representation to illustrate the dimensioning of the adhesive film to be lined with the woven fabric web and which is provided with a tear-off film (liner).

FIG. 12 shows the dimensioning of adhesive-free zones 70A, which lie congruent beneath tabs 200E, with the aid of zero line 310 which is formed by contrast-rich warp thread K.

According to the inventive method, the separation of individual moisture sensors 200 takes place with a laser. The advantage of a laser lies in the fact that fraying of the threads is avoided when the moisture sensors are cut out, since the edges are sealed by the thermal effect of the laser. Further advantages lie in the particularly high degree of accuracy that results from the precise guidance of the laser beam and its small diameter. Different geometries can also easily be cut with the laser. The sensors can alternatively also be separated by ultrasound punching. Ultrasound punching can take place for example at a frequency of 40 kHz.

The exact guidance of the laser or the ultrasound punch requires a precise determination of the position of contour 250 of moisture sensor 200. With the method according to the present invention, cross-shaped marking elements 320 are provided for the position determination, said marking elements being woven between moisture sensors 200. Cross-shaped marking elements 320 are formed by conductive warp and weft threads K, S which intersect one another. These conductive threads are laid at the surface of woven fabric web 300, so that they can be detected by an automated image processing system. Alternatively, the marking elements can again be formed by non-conductive, but contrast-rich threads.

Figure 13:
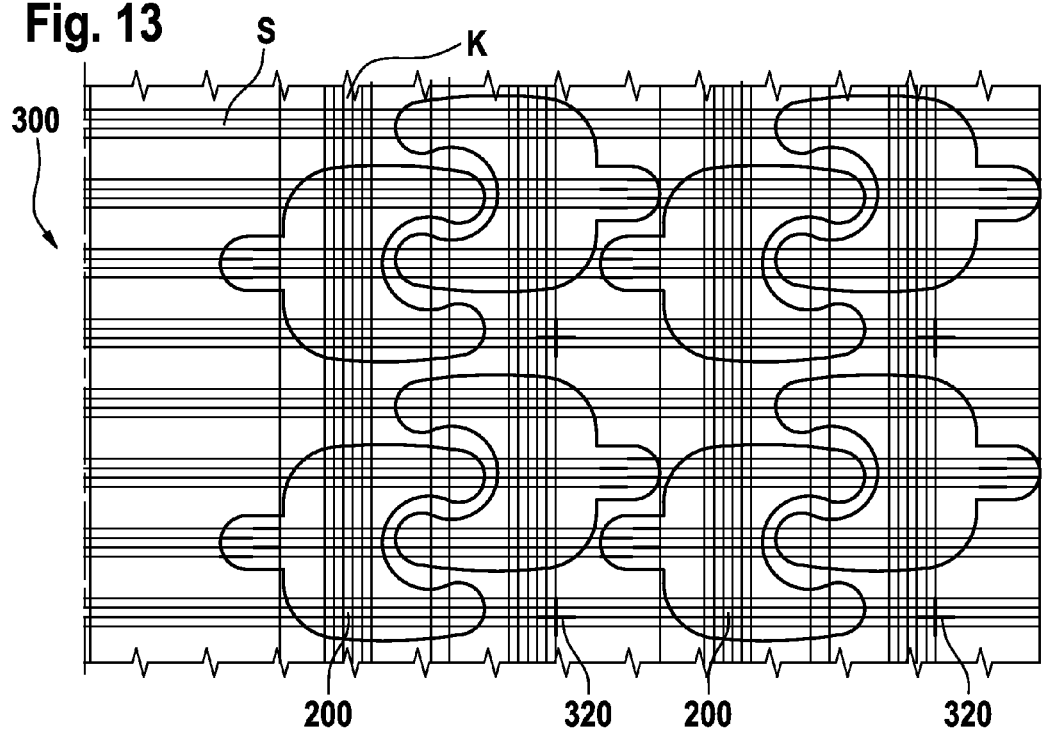
FIG. 13 shows a representation to illustrate the arrangement of marking elements for the position recognition of the moisture sensors on the woven fabric web.
Figure 14:
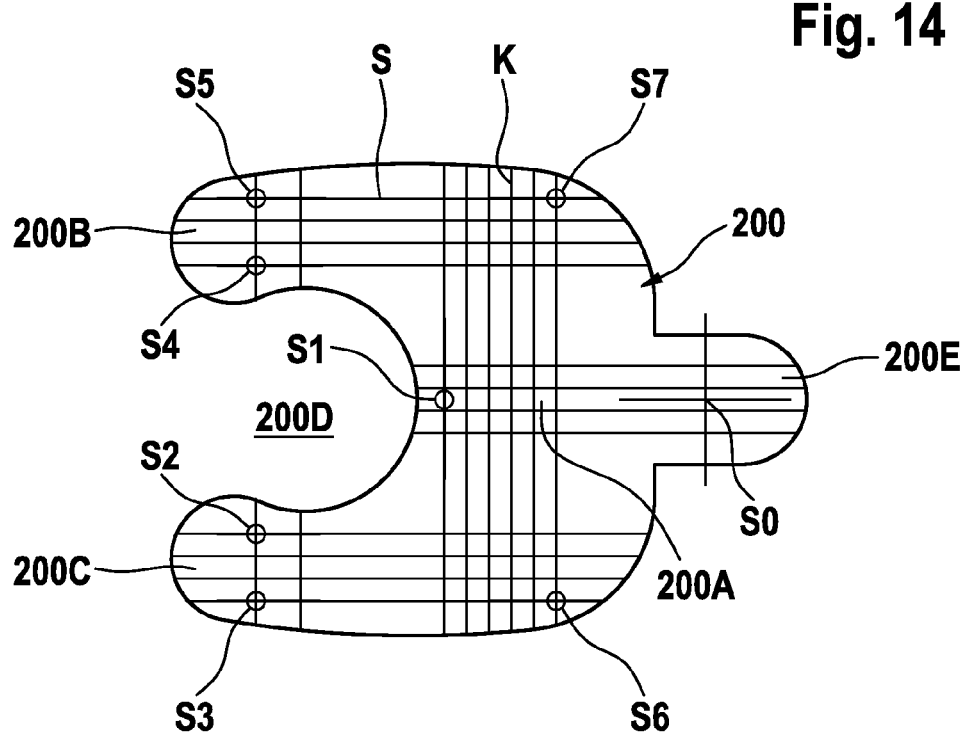
FIG. 14 shows a representation to illustrate the control points for checking the moisture sensors after the separation.

FIG. 13 shows the arrangement of cross-shaped marking elements 320 on woven fabric web 300 outside moisture sensors 200. Cross-shaped marking elements 320, with which the position of the moisture sensors is marked, are detected by a camera system and processed with an image processing system. These devices are known to the person skilled in the art. After the separation of the moisture sensors by means of the laser, a control of the moisture sensors takes place within the process (in-process control (IPC)). A check is carried out to establish whether predetermined control points on moisture sensor 200 lie within the cutting contour. The predetermined control points are the points of intersection of intersecting warp and weft threads K, S. These control points are denoted by S1 to S7 in FIG. 14. Points of intersection S1-S7 are detected by a camera system when the sensors are cut out and a check is carried out with the image processing system to establish whether the points of intersection related to a predetermined zero point S0, which lies in tab 200E of moisture sensor 200, lie within a defined tolerance field. Minimum and maximum values for the coordinates of points of intersection S can be stored in the image processing system. The deviations of the actual values from the setpoint values are calculated by the image processing system, it being concluded that there is a faulty sensor if the deviations exceed predetermined threshold values. In this case, the corresponding moisture sensors are rejected. The in-process control can also include a check of the electrical properties of the strip conductors.

For this purpose, a check is made to establish whether the electrical resistance between strip conductors L1A/L1E lies within a predetermined setpoint value range and whether the resistance between strip conductors L2A/L2E lies within a predetermined setpoint value range. Moreover, a check is made to establish whether any short-circuit exists between strip conductors L1A/L2A and L1E/L2E.

After the separation and check, the moisture sensors are packaged. Since the tear-off film (liner) in the region of the tab is not glued to the adhesive film, since the adhesive film is free from adhesive at the rear side in the region of the tab, the tear-off film can easily be gripped in the region of the tab and torn off from the moisture sensor. The section of the liner in the region of the tab thus serves as a tear-off aid. In order to allow this section to be gripped easily, the liner is folded through 180° in the region of the tab.

Figure 15:
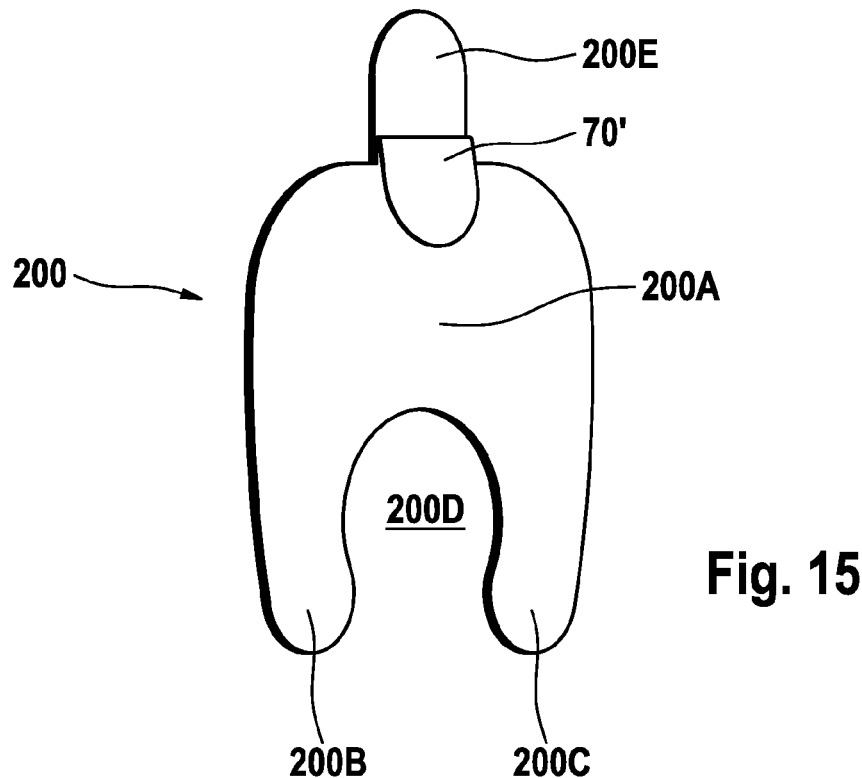
FIG. 15 shows the moisture sensor with the terminal tab in a rear view.

FIG. 15 shows a rear view of moisture sensor 200 with tab 200E and tear-off film (liner) 70' folded in the region of tab 200E. The line at which tear-off film 70' is folded runs parallel to the line at which tab 200E adjoins central region 200A of moisture sensor 200, i.e., parallel to the line which separates the adhesive-free region from the region of adhesive film 70 provided with adhesive (FIG. 11). The bending edge of the folded liner section extends, for example, by 2 mm, into the tab and thus enables traversing of the adhesive-free edge due to tolerances. The tear-off film (liner) projecting in the region of the tab can easily be gripped, so that the liner can easily be torn off from the adhesive film. Since the moisture sensor does not adhere to the patient's skin in the region of the tab on account of the absence there of the adhesive layer, the moisture sensor can also easily be gripped by the tab after use and pulled off from the skin.

What is claimed is:

1. A method for producing a plurality of moisture sensors for a device for monitoring a patient access, the method comprising:

disposing non-conductive warp threads, non-conductive weft threads, conductive warp threads and conductive weft threads in a textile two-dimensionally extending structure such that spatially demarcatable structures of electrical strip conductors are created, wherein a plurality of individual moisture sensors are woven beside one another normal to a production direction on a common woven fabric web; and after the weaving, separating the individual moisture sensors from one another, wherein the moisture sensors of a group of moisture sensors, which are woven beside one another normal to the production direction, are disposed interlaced with respect to one another, wherein the moisture sensors each comprise a central region with two legs which laterally surround a central cutout, wherein the moisture sensors on the woven fabric web are disposed offset with respect to one another, such that in each case a leg of a moisture sensor engages in a cutout of another moisture sensor, wherein a lateral offset of the moisture sensors corresponds to a spacing of individual groups of warp and weft threads with which the strip conductors are created on the central region and the two legs of the moisture sensors.

2. The method according to claim 1, further comprising weaving a compensation strip running normal to the production direction between a preceding group of moisture sensors, which are woven beside one another normal to the production direction, and a subsequent group of moisture sensors, which are woven beside one another normal to the production direction.

3. The method according to claim 1, wherein intersecting conductive warp threads and weft threads are disposed for the formation of the strip conductor structures such that the warp and weft threads make contact at individual points of intersection.

4. The method according to claim 1, wherein the strip conductor structures of the individual moisture sensors are formed from groups of conductive warp threads, which each comprise a plurality of conductive warp threads running in a first direction, and groups of conductive weft threads, which each comprise a plurality of conductive weft threads running beside one another in a direction at right angles to the first direction, wherein at least one of the groups of warp threads are disposed with an equal spacing from one another and the groups of weft threads are disposed with an equal spacing from one another.

5. The method according to claim 4, wherein the conductive warp threads run in the production direction and the conductive weft threads run normal to the production direction.

6. The method according to claim 1, wherein the strip conductor structures of the moisture sensors are each formed by three groups of weft threads and two groups of warp threads.

7. The method according to claim 6, wherein the groups of the weft threads have the same number of weft threads.

8. The method according to claim 7, wherein the groups of warp threads have a different number of warp threads.

9. The method according to claim 6, wherein the groups of weft threads are disposed with an equal spacing.

10. The method according to claim 1, further comprising at least one of weaving marking elements running in the production direction and weaving cross-shaped marking elements between the moisture sensors.

11. The method according to claim 10, wherein the marking elements are formed by at least one of conductive warp and weft threads which are laid at the surface of the woven fabric.

12. The method according to claim 1, wherein on the rear side of the woven fabric web facing a patient's skin a two-sided adhesive film is applied, which is provided with a tear-off film that can be torn off at the rear side that lies on the patient's skin, the tear-off film protecting an adhesive layer at the rear side of the adhesive film, wherein the adhesive film comprises at predetermined intervals at the rear side, which is to be stuck onto the patient's skin, sections in which the adhesive film is free from adhesive.

13. The method according to claim 12, further comprising, after the separation of the individual moisture sensors, folding the section of the tear-off film not glued to the adhesive film.

14. The method according to claim 1, wherein the moisture sensors each comprise tabs on which the strip conductors form terminal contacts.

15. The method according to claim 1, wherein at least a part of the non-conductive warp threads, non-conductive weft threads, conductive warp threads and conductive weft threads are provided with a spinning preparation.

16. The method according to claim 1, wherein the individual moisture sensors are separated from one another by means of a laser.

17. The method according to claim 1, further comprising:
after the separation of the individual moisture sensors, checking the position of defined control points on the moisture sensor by means of an image processing system, wherein it is determined that there is a faulty moisture sensor when the control points do not lie within a predetermined tolerance field.

18. The method according to claim 17, wherein the control points are the points of intersection of intersecting conductive warp and weft threads.

* * * * *